US010294333B2

(12) United States Patent
Liu et al.

(10) Patent No.: US 10,294,333 B2
(45) Date of Patent: May 21, 2019

(54) ROOM TEMPERATURE CURABLE SILOXANE-BASED GELS

(71) Applicant: 3M INNOVATIVE PROPERTIES COMPANY, St. Paul, MN (US)

(72) Inventors: Junkang J. Liu, Woodbury, MN (US); Hironobu Ishiwatari, Tokyo (JP); Siegfried K. Welke, Erkrath (DE); Yoshiteru Kakinuma, Tokyo (JP)

(73) Assignee: 3M Innovative Properties Company, St. Paul, MN (US)

( * ) Notice: Subject to any disclaimer, the term of this patent is extended or adjusted under 35 U.S.C. 154(b) by 163 days.

(21) Appl. No.: 14/650,608

(22) PCT Filed: Dec. 4, 2013

(86) PCT No.: PCT/US2013/073070
§ 371 (c)(1),
(2) Date: Jun. 9, 2015

(87) PCT Pub. No.: WO2014/093093
PCT Pub. Date: Jun. 19, 2014

(65) Prior Publication Data
US 2015/0376345 A1 Dec. 31, 2015

Related U.S. Application Data

(60) Provisional application No. 61/736,107, filed on Dec. 12, 2012.

(51) Int. Cl.
| | | |
|---|---|---|
| *C08G 77/44* | (2006.01) | |
| *C08G 77/16* | (2006.01) | |
| *C08L 83/06* | (2006.01) | |
| *C08K 5/544* | (2006.01) | |
| *C09J 183/04* | (2006.01) | |
| *C09J 183/10* | (2006.01) | |
| *C09J 7/40* | (2018.01) | |
| *C08L 83/04* | (2006.01) | |
| *A61L 24/04* | (2006.01) | |
| *C08J 3/28* | (2006.01) | |
| *C09K 3/10* | (2006.01) | |
| *C08L 83/00* | (2006.01) | |

(52) U.S. Cl.
CPC ............ *C08G 77/44* (2013.01); *A61L 24/046* (2013.01); *C08J 3/28* (2013.01); *C08K 5/544* (2013.01); *C08L 83/00* (2013.01); *C08L 83/04* (2013.01); *C09J 7/40* (2018.01); *C09J 183/04* (2013.01); *C09J 183/10* (2013.01); *C09K 3/1018* (2013.01); *C08G 77/16* (2013.01); *C08G 2220/00* (2013.01); *C08L 2205/02* (2013.01)

(58) Field of Classification Search
None
See application file for complete search history.

(56) References Cited

U.S. PATENT DOCUMENTS

| | | | |
|---|---|---|---|
| 3,645,835 A | 2/1972 | Hodgson | |
| 4,595,001 A | 6/1986 | Potter | |
| 4,831,070 A | 5/1989 | McInally | |
| 5,088,483 A | 2/1992 | Heinecke | |
| 5,160,315 A | 11/1992 | Heinecke | |
| 5,482,988 A * | 1/1996 | Ulman | A61K 9/7069 524/266 |
| 5,891,076 A | 4/1999 | Fabo | |
| 6,828,355 B1 * | 12/2004 | Chu | C09J 183/04 522/148 |
| 6,881,807 B2 | 4/2005 | Terada | |
| 6,939,925 B2 * | 9/2005 | Sakamoto | C08G 77/44 524/266 |
| 2005/0282977 A1 | 12/2005 | Stempel | |
| 2007/0202245 A1 | 8/2007 | Gantner | |
| 2010/0331785 A1 | 12/2010 | Fabo | |
| 2011/0028647 A1 | 2/2011 | Sixt | |
| 2011/0106030 A1 | 5/2011 | Scholz | |
| 2011/0112458 A1 | 5/2011 | Holm | |
| 2011/0206923 A1 | 8/2011 | Liu | |
| 2011/0206924 A1 | 8/2011 | Liu | |
| 2011/0212325 A1 | 9/2011 | Determan | |
| 2012/0029455 A1 | 2/2012 | Perez-Foullerat | |
| 2012/0095109 A1 | 4/2012 | Garaud | |
| 2012/0135225 A1 | 5/2012 | Colas | |
| 2012/0270976 A1 * | 10/2012 | Kawakami | B01D 53/228 524/217 |

FOREIGN PATENT DOCUMENTS

| | | | |
|---|---|---|---|
| CA | 711756 | 6/1965 | |
| EP | 239099 A2 * | 9/1987 | ............ C09J 7/00 |
| EP | 2001424 | 12/2008 | |
| WO | WO 2008-057155 | 5/2008 | |
| WO | WO 2011-003054 | 1/2011 | |
| WO | WO 2011-022199 | 2/2011 | |
| WO | WO 2011-136977 | 11/2011 | |
| WO | WO 2012-069794 | 5/2012 | |

OTHER PUBLICATIONS

International Search Report for PCT International Application No. PCT/US2013/073070 dated Feb. 11, 2014, 3 pages.

\* cited by examiner

*Primary Examiner* — Frank D Ducheneaux
(74) *Attorney, Agent, or Firm* — Jeffrey M. Olofson

(57) ABSTRACT

Siloxane-based gel compositions are prepared from room temperature condensation curable mixtures that include 0.5-45% by weight silicone resin with at least two hydroxyl groups, 99.5-55% by weight of at least one silanol-terminated siloxane fluid, and a co-curable compound with an amino group. The siloxane-based gel compositions can be used as adhesives or sealants in medical articles.

22 Claims, No Drawings

ROOM TEMPERATURE CURABLE SILOXANE-BASED GELS

FIELD OF THE DISCLOSURE

This disclosure relates to siloxane-based gels that may be used to form adhesive articles, such as tapes, or sealant articles, that are useful in medical applications.

BACKGROUND

A wide range of adhesive articles are used in medical applications. These adhesive articles include gels used to attach electrodes and other sensing devices to the skin of a patient, a wide range of tapes to attach medical devices to a patient, and adhesive dressings used to cover and protect wounds.

Many of the adhesive articles use pressure sensitive adhesives. Pressure sensitive adhesives are well known to one of ordinary skill in the art to possess certain properties at room temperature including the following: (1) aggressive and permanent tack, (2) adherence with no more than finger pressure, (3) sufficient ability to hold onto an adherend, and (4) sufficient cohesive strength to be removed cleanly from the adherend. Materials that have been found to function well as pressure sensitive adhesives are polymers designed and formulated to exhibit the requisite viscoelastic properties resulting in a desired balance of tack, peel adhesion, and shear strength. The most commonly used polymers for preparation of pressure sensitive adhesives are natural rubber, synthetic rubbers (e.g., styrene/butadiene copolymers (SBR) and styrene/isoprene/styrene (SIS) block copolymers), various (meth)acrylate (e.g., acrylate and methacrylate) copolymers, and silicones.

One problem with using adhesive articles for medical applications is that the removal of adhesive article can cause trauma to the skin. This is particularly troublesome in patients with sensitive skin, such as infants and the elderly, and can become severe with chronic patients where adhesive articles are repeatedly attached and removed over a long term period.

Various attempts have been made to mitigate this problem with adhesive articles. In particular, health care professionals utilized removal techniques to mitigate skin trauma. One way to mitigate trauma to the skin is to remove the adhesive article using a slow peel at a high angle to avoid stretching the skin. Another way to mitigate trauma, when the adhesive article is stretchable, is to pull straight out (as close to a 0° angle as possible) to induce stretch releasing of the adhesive layer from the skin. Also, manufactures of adhesive articles have developed articles that mitigate skin trauma. So called "gentle-to-skin adhesives" have been developed that provide sufficient adhesion to skin to adhere the adhesive article to the skin, but do not strip of skin cells significantly when removed.

A variety of gentle-to-skin adhesives and dressings that use gentle-to-skin adhesives have been described. A gentle-to-skin adhesive is described in US Patent Publication No. 2011/0212325 (Determan et al.) which describes an electron beam and gamma radiation crosslinked silicone gel adhesive that may use either nonfunctional or functional poly diorganosiloxanes. In the European Patent No. EP 2,001,424 (Cotton) adhesive laminate dressings are described that include a hydrophobic gel adhesive useful as the skin contact layer, and also containing a structural layer having the gel adhesive on one side and a pressure sensitive adhesive on the other side. Also, U.S. Pat. No. 5,891,076 (Fabo) describes a hypertrophic scar dressing that includes silicone-gel on that side of the dressing which lies against the user's skin and a flexible carrier sheet embodied within the silicone-gel such tht the gel forms continuous layers on both sides of the carrier, and US Patent Publication No. 2010/0331785 (Fabo et al.) describes a dressing that includes a liquid impermeable film layer coated with a skin friendly adhesive on the side intended to adhere to the skin.

A variety of silicone pressure sensitive adhesives and blends of silicone pressure sensitive adhesives have been described. In U.S. Pat. No. 4,831,070 (McInally et al.) a composition suitable for use as a medical adhesive is described with contains a curable mixture of (A) a copolymer containing triorganosiloxy units and (B) a polydiorganosiloxane fluid containing hydroxyl groups, an organosilicon compound with more than two silicon-bonded alkoxy groups per molecule, and a condensation catalyst. In the Canadian Patent Publication No. 711,756 (Pail), a pressure sensitive adhesive is prepared by heating a mixture at a temperature above 100° C. of (1) 45-75 weight % of a resin copolymer with $SiO_2$ and $R_3SiO_{1/2}$ units; (2) 25-55 weight % of a hydroxyl endblocked polydiorganosiloxane fluid, and (3) 0.001-5 weight % of an aliphatic organic amine compound. In US Patent Publication No. 2012/0095109 (Garaud et al.) adhesive films include (a) a polyoransiloxane resin composed of M and Q units, (d) a hydrosilation catalyst and at least one of (b) a polyorganosiloxane compound having at least 2 Si—H groups, or (c) a telechelic polyorganosiloxane compound having terminal Si—H groups. In US Patent Publication No. 2011/0028647 (Sixt et al.) room temperature crosslinkable materials are described that are based on organosilicon compounds and a catalyst containing a metal of the main or subgroup I or II in conjunction with an inorganic acid. US Patent Publication 2007/0202245 (Gantner et al.) describes a method for adhering a medical substrate to a human or animal using a silicone gel containing a hydroxyl substituted siloxane resin. US Patent Publication 2005/0282977 (Stempel et al.) describes a pressure sensitive adhesive composition comprising a blend of (1) a gel comprising a copolymer of an organosiloxane and siloxane having a plurality of reactive functionalities and a crosslinking agent, and (2) a pressure sensitive adhesive that is non-reactive with the gel. In U.S. Pat. No. 6,881,807 (Terada et al.) a curable silicone gel comprising (A) a polyorganosiloxane, (C) an addition-reaction platinum catalyst, (D) an organosilicon compound, and (E) an organic titanium compound.

Medical articles are described in US Patent Publication No. 2012/0029455 (Perez-Foullerat et al.), which describes wound dressings with gel adhesives, and US Patent Publication No. 2012/0135225 (Colas et al.) which describes a multi-layer transdermal patch comprising a non-curing pressure sensitive adhesive that has a therapeutic agent blended with it. Medical sealants are described in PCT Publication No. 2012/069794 (Phillips et al.) which describes a two part tissue sealant with part A comprising alkenyl-group containing prepolymers, and part B comprising prepolymers containing Si—H groups, and a catalyst.

SUMMARY

Disclosed herein are siloxane-based gel compositions, articles containing them and methods of preparing articles containing siloxane-based gel compositions.

In some embodiments, gel compositions comprise the reaction product of a condensation curable mixture comprising 0.5-45% by weight silicone resin comprising at least two hydroxyl groups, 99.5-55% by weight of at least one silanol-terminated siloxane fluid, and a co-curable compound comprising an amino group, wherein the condensation curable mixture is curable at room temperature.

Also described are articles comprising a layer of adhesive gel disposed on at least a portion of at least one major surface of the substrate, the adhesive gel comprising the reaction product of a condensation curable mixture comprising 0.5-45% by weight silicone resin comprising at least two hydroxyl groups, 99.5-55% by weight of at least one silanol-terminated siloxane fluid, and a co-curable compound comprising an amino group, wherein the condensation curable mixture is curable at room temperature.

Methods for preparing medical articles comprise providing a condensation curable gel precursor composition comprising 0.5-45% by weight silicone resin comprising at least two hydroxyl groups, 99.5-55% by weight of at least one silanol-terminated siloxane fluid, and a co-curable compound comprising an amino group, wherein the condensation curable mixture is curable at room temperature, applying the condensation curable gel precursor composition to a substrate, and permitting the condensation curable gel precursor composition to cure at room temperature to form a gel. The formed gel articles may be adhesives or sealants.

DETAILED DESCRIPTION

The widespread use of adhesives, especially pressure sensitive adhesives, in medical applications has led to the development of adhesives and adhesive articles that are gentle to the skin. Some of these adhesives are pressure sensitive adhesives and others are gel adhesives. The application of pressure sensitive adhesives, including silicone pressure sensitive adhesives, for adhering to skin is known in the art and many examples are commercially available. However, some pressure sensitive adhesives have limited application for adhesion to skin. For instance, skin damage may result during the removal of a pressure sensitive adhesive that exhibits surface adhesion to skin that is too high. Alternatively, if the surface adhesion to skin is reduced, the pressure sensitive adhesive may lack sufficient holding power to be useful or will lose the room temperature tackiness that makes easy application of the adhesive possible. Additionally, some pressure sensitive adhesives that are relatively rigid or non-conformable compared to skin typically result in considerable patient discomfort during use. Also, even adhesives that have a measured low peel adhesion to skin may cause discomfort during removal, e.g., if the adhesive becomes surface attached around hair.

Silicone gel (crosslinked poly dimethylsiloxane ("PDMS")) materials have been used for dielectric fillers, vibration dampers, and medical therapies for promoting scar tissue healing. Lightly crosslinked silicone gels are soft, tacky, elastic materials that comprise relatively high levels of fluids (liquids). Silicone gels are typically softer than silicone pressure sensitive adhesives, resulting in less discomfort when adhered to skin. The combination of reasonable adhesive holding power on skin and low skin trauma upon removal, make silicone gels suitable for gentle to skin adhesive applications.

Silicone gel adhesives provide good adhesion to skin with gentle removal force and have the ability to repositioned. Examples of commercially available silicone gel adhesive systems include products marketed with the trade names: Dow Corning MG 7-9850, WACKER 2130, BLUESTAR 4317 and 4320, and NUSIL 6345 and 6350. These gentle to the skin adhesives are formed by an addition cure reaction between vinyl-terminated PDMS and hydrogen terminated PDMS, in the presence of a hydrosilation catalyst (e.g., platinum complex). Vinyl-terminated and hydrogen terminated PDMS chains are referred to as 'functionalized' silicones due to their specific chemical moieties. Individually, such functional silicones are generally not reactive; however, together they form a reactive silicone system. Additionally, silicone resins (tackifiers sometimes referred to as "silicate resins") and PDMS with multiple hydrogen functionalities (crosslinkers) can be formulated to modify the adhesive properties of the gel.

There are downsides to the use of these types of materials. For example, they required the use of specialized "functionalized" silicone materials. Also, they typically required the use of a catalyst, often a metal-containing catalyst such as platinum or palladium catalysts. These catalysts are expensive and leave metal-containing residues in the cured compositions. An alternative to the catalyst-promoted curing of such silicone materials is the use of free radical polymerization to cure or crosslink the silicone pressure sensitive adhesive or gel formulations. These polymerizations require initiation by a free radical source, such as, for example, the high temperature degradation of organic peroxides. This curing technique is undesirable due to the acidic residues left in the film from the curing chemistry, which are corrosive and unsuitable for skin contact.

Therefore, it is desirable that siloxane-based gel adhesives and sealants could be prepared to cure and crosslink at room temperature without generating undesirable catalyst or initiator residues. Additionally, it is desirable that the siloxane-based gel adhesives and sealants be formed from siloxane-based starting materials that do not require specialized functionalization.

This disclosure describes siloxane-based gel compositions that are the product of a condensation reaction. In this reaction, two silanol groups (that is to say, terminal —SiOH groups) condense to form —Si—O—Si— linkages and a molecule of water ($H_2O$). The siloxane-based gels are the reaction product of a condensation curable mixture comprising 0.5-45% by weight silicone resin comprising at least two hydroxyl groups, 99.5-55% by weight of at least one silanol-terminated siloxane fluid, and a co-curable compound comprising an amino group. The co-curable compound comprising an amino group is present to help to catalyze the condensation reaction, but since it is co-curable, that is to say it becomes chemically attached to the polymer matrix, it does produce catalyst residue as in the case of metal-based catalysts or free radical intitiators. These gel compositions can be used as adhesives or as sealants.

These siloxane-based gel adhesives and sealants have excellent wetting and flow characteristics, due to the very low glass transition temperature (Tg) and modulus of the polysiloxane network which results in sufficient adhesive holding power on the rough skin surface due to mechanical interlock and energy dissipation within the gel adhesive. Additionally, the low surface adhesion of silicone gels prevent the adhesive from tightly attaching to hair or skin cells during skin wear, further reducing the instance of pain during removal. This results in minimal to no skin trauma upon removal.

As used herein, the term "gel" refers to a semi-solid crosslinked matrix containing a liquid or a fluid. The gels may be adhesives or sealants. As used herein, the term "gel adhesive" refers to a tacky semi-solid crosslinked matrix containing a liquid or a fluid that is capable of adhering to one or more substrates. As used herein, the term "gel sealant" refers to a curable mixture that upon curing forms a continuous gel layer that is capable of forming a seal over or around, for example, a wound, a cut, an incision or the like.

The term "adhesive" as used herein refers to polymeric compositions useful to adhere together two adherends. Examples of adhesives are pressure sensitive adhesives.

Pressure sensitive adhesive compositions are well known to those of ordinary skill in the art to possess properties including the following: (1) aggressive and permanent tack, (2) adherence with no more than finger pressure, (3) sufficient ability to hold onto an adherend, and (4) sufficient cohesive strength to be cleanly removable from the adherend. Materials that have been found to function well as pressure sensitive adhesives are polymers designed and formulated to exhibit the requisite viscoelastic properties resulting in a desired balance of tack, peel adhesion, and shear holding power. Obtaining the proper balance of properties is not a simple process.

The term "siloxane or siloxane-based" as used herein refers to polymers that contain units with dialkyl or diaryl siloxane ($-SiR_2O-$) repeating units. The siloxane-based polymers may be segmented copolymers or polysiloxane polymers. The terms silicone and siloxane are used interchangeably.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl. Simple alkyl groups are abbreviated herein as methyl=Me, ethyl=Et, n-propyl=Pr.

The term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl. The simple aryl group phenyl is abbreviated herein as Ph.

The term "alkylene" refers to a divalent group that is a radical of an alkane. The alkylene can be straight-chained, branched, cyclic, or combinations thereof. The alkylene often has 1 to 20 carbon atoms. In some embodiments, the alkylene contains 1 to 18, 1 to 12, 1 to 10, 1 to 8, 1 to 6, or 1 to 4 carbon atoms. The radical centers of the alkylene can be on the same carbon atom (i.e., an alkylidene) or on different carbon atoms.

The term "heteroalkylene" refers to a divalent group that includes at least two alkylene groups connected by a thio, oxy, or $-NR-$ where R is alkyl. The heteroalkylene can be linear, branched, cyclic, substituted with alkyl groups, or combinations thereof. Some heteroalkylenes are poloxyyalkylenes where the heteroatom is oxygen such as for example,

The term "arylene" refers to a divalent group that is carbocyclic and aromatic. The group has one to five rings that are connected, fused, or combinations thereof. The other rings can be aromatic, non-aromatic, or combinations thereof. In some embodiments, the arylene group has up to 5 rings, up to 4 rings, up to 3 rings, up to 2 rings, or one aromatic ring. For example, the arylene group can be phenylene.

The term "aralkylene" refers to a divalent group of formula $-R^a-Ar^a-$ where $R^a$ is an alkylene and $Ar^a$ is an arylene (i.e., an alkylene is bonded to an arylene).

The term "condensable end group" refers to a monovalent self-reactive terminal group of general formula: $-SiR_2(OX)$, where R is an alkyl group and X is a H or R group.

Disclosed herein are gels comprising the reaction product of a condensation curable mixture comprising 0.5-45% by weight of a silicone resin with at least two hydroxyl groups, 99.5-55% by weight of at least one silanol-terminated siloxane fluid, and a co-curable compound comprising an amino group. The condensation curable mixture is curable at room temperature.

The condensation curable mixture includes 0.5-45% by weight of silicone resin comprising at least two hydroxyl groups. Suitable silicone resins include the commercially available tackifying resins, that are often referred to as "silicate tackifying resins" (the term "silicate resin" has been replaced in common parlance by the more correct term "silicone resin", but the terms are used interchangeably herein). The hydroxyl groups on the silicone resins permits them to co-condense with the silanol-terminated siloxane fluid and thus become incorporated into the crosslinked siloxane polymer network.

Suitable silicone resins include those resins composed of the following structural units M (i.e., monovalent $R'_3SiO_{1/2}$ units), D (i.e., divalent $R'_2SiO_{2/2}$ units), T (i.e., trivalent $R'SiO_{3/2}$ units), and Q (i.e., quaternary $SiO_{4/2}$ units), and combinations thereof. Typical exemplary silicone resins include MQ silicone resins, MQD silicone resins, and MQT silicone resins. These silicone resins usually have a number average molecular weight in the range of 100 to 50,000-g/mole, e.g., 500 to 15,000 g/mole and generally R' groups are methyl.

MQ silicone resins are copolymeric resins where each M unit is bonded to a Q unit, and each Q unit is bonded to at least one other Q unit. Some of the Q units are bonded to only other Q units. However, some Q units are bonded to hydroxyl radicals resulting in $HOSiO_{3/2}$ units (i.e., "$T^{OH}$" units), thereby accounting for some silicon-bonded hydroxyl content of the silicone resin.

The level of silicon bonded hydroxyl groups (i.e., silanol) on the MQ resin may be reduced to no greater than 1.5 weight percent, no greater than 1.2 weight percent, no greater than 1.0 weight percent, or no greater than 0.8 weight percent based on the weight of the silicate tackifying resin. This may be accomplished, for example, by reacting hexamethyldisilazane with the silicate tackifying resin. Such a reaction may be catalyzed, for example, with trifluoroacetic acid. Alternatively, trimethylchlorosilane or trimethylsilylacetamide may be reacted with the silicate tackifying resin, a catalyst not being necessary in this case.

Suitable silicone resins are commercially available from sources such as Dow Corning (e.g., DC 2-7066), Momentive Performance Materials (e.g., SR545 and SR1000), and Wacker Chemie AG (e.g., BELSIL TMS-803).

The condensation curable mixture includes 0.5-45% by weight of the silicone resin comprising at least two hydroxyl groups. More typically the condensation curable mixture includes 1.0-30% by weight or even 1.0-20% by weight of the silicone resin comprising at least two hydroxyl groups. While not wishing to be bound by theory, it is believed that if the level of silicone resin is too high the adhesive flow characteristics will be limited and thus the adhesive would be less suitable for the desired skin adhesion applications.

The condensation curable mixture also includes 99.5-55% by weight of at least one silanol-terminated siloxane material. In general, these siloxane materials may be oils, fluids, gums, elastomers, or resins, e.g., friable solid resins. Generally, lower molecular weight, lower viscosity materials are referred to as fluids or oils, while higher molecular weight, higher viscosity materials are referred to as gums; however, there is no sharp distinction between these terms. Elastomers and resins have even higher molecular weights than gums, and typically do not flow. As used herein, the terms "fluid" and "oil" refer to materials having a dynamic viscosity at 25° C. of no greater than 1,000,000 mPa·sec (e.g., less than 600,000 mPa·sec), while materials having a dynamic viscosity at 25° C. of greater than 1,000,000 mPa·sec (e.g., at least 10,000,000 mPa·sec) are referred to as "gums".

A wide variety of silanol-terminated siloxane fluids are suitable for use with the gel compositions of this disclosure. Generally, the silanol-terminated siloxane fluids are linear materials described by Formula 1 below:

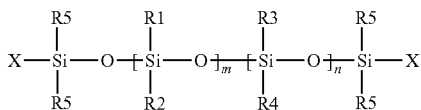

Formula 1
wherein R1, R2, R3, and R4 are independently selected from the group consisting of an alkyl group, an aryl group and a functional group, each R5 is an alkyl group, each X is a hydroxyl group, and n and m are integers, and at least one of m or n is not zero. In some embodiments, one or more of the alkyl or aryl groups may contain a halogen substituent, e.g., fluorine. For example, in some embodiments, one or more of the alkyl groups may be —$CH_2CH_2C_4F_9$.

In other embodiments, each R5 is a methyl such that the poly diorganosiloxane material is terminated by dimethylsilanol groups. In some embodiments, R1 and R2 are alkyl groups and n is zero, i.e., the material is a poly(dialkylsiloxane). In some embodiments, the alkyl group is a methyl group, i.e., poly(dimethylsiloxane) ("PDMS"). In some embodiments, R1 is an alkyl group, R2 is an aryl group, and n is zero, i.e., the material is a poly(alkylarylsiloxane). In some embodiments, R1 is methyl group and R2 is a phenyl group, i.e., the material is poly(methylphenylsiloxane). In some embodiments, R1 and R2 are alkyl groups and R3 and R4 are aryl groups, i.e., the material is a poly(dialkyldiarylsiloxane). In some embodiments, R1 and R2 are methyl groups, and R3 and R4 are phenyl groups, i.e., the material is poly(dimethyldiphenylsiloxane).

In some embodiments, the nonfunctionalized poly diorganosiloxane materials may be branched. For example, one or more of the R1, R2, R3, and/or R4 groups may be a linear or branched siloxane with alkyl or aryl (including halogenated alkyl or aryl) substituents and terminal R5 groups.

In some commercially available embodiments, R1, R2, R3, R4, and R5 are all methyl groups, making the material a polydimethyl siloxane or PDMS material. In other embodiments, at least some of the R1, R2, R3, and R4 are aryl groups.

Recently, gentle to skin adhesives have been described in US Patent Publication No. 2011/0212325 (Determan et al.) that can be prepared from non-functionalized polysiloxane materials. These materials are ones described by Formula 1 with X=R5, and ones described by Formula 1 where X=OH. The materials where X=OH are considered to be "Non-functionalized materials" in this reference because the hydroxyl groups are not used as "functional groups", that is to say that the polymerization reaction does not involve reaction with the hydroxyl groups. These "non-functional materials" have been found to polymerize upon exposure to electron beam or gamma radiation generate siloxane networks.

Many suitable silanol-terminated siloxane fluids are commercially available. Numerous examples of materials are commercially available from, for example, Gelest, Inc. Morrisville, Pa., Dow Corning, Midland Mich., and Wacker Chemie AG, Munich, Germany. Particularly suitable examples include the silanol terminated PDMS (polydimethyl siloxane), commercially available as XIAMETER OHX-4070, from Dow Corning, Midland, Mich., and the hydroxyl functional PDMS commercially available as 350N from Wacker Chemie AG, Munich, Germany.

As stated above, gels include a semi-solid crosslinked matrix containing a liquid or a fluid. In some embodiments, the liquid or fluid present in the gels of the present disclosure may be unreacted silanol-terminated siloxane fluid. In other embodiments, the liquid or fluid present in the gels of the present disclosure may be one or more added unreactive siloxane fluids. These fluids have the general structure shown in Formula 1A below:

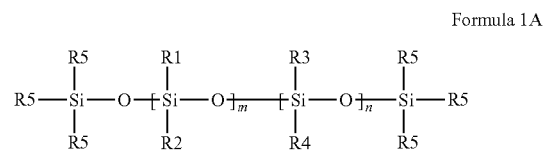

Formula 1A wherein R1, R2, R3, and R4 are independently selected from the group consisting of an alkyl group, an aryl group and a functional group, each R5 is an alkyl group, and n and m are integers, and at least one of m or n is not zero. In some embodiments, one or more of the alkyl or aryl groups may contain a halogen substituent, e.g., fluorine. For example, in some embodiments, one or more of the alkyl groups may be —$CH_2CH_2C_4F_9$.

The unreactive siloxane fluid, as the term suggests, are siloxane fluids that do not participate in the curing reaction and are not incorporated into the formed crosslinked siloxane matrix.

The addition of unreactive siloxane fluid, while optional, may be desirable for a number of reasons. The presence of unreactive siloxane fluid ensures that siloxane fluid remains in the gel, whereas relying on the presence of unreacted silanol-terminated siloxane fluid can produce variable levels of siloxane fluid present in the gel due to variations in the extent of reaction. Additionally, the addition of one or more unreactive siloxane fluid provides the ability of adding siloxane fluids with a viscosity different from the silanol-terminated siloxane fluid and thus control the properties of the gel.

Typically the gels of this disclosure comprise at least 0.5% by weight of extractable siloxane fluid. As pointed out above, this extractable siloxane fluid can be unreacted silanol-terminated siloxane fluid, added unreactive siloxane fluid, or a combination thereof. In some embodiments, the level of extractable siloxane fluid can be as high as 40% by weight.

The condensation curable mixture also includes a co-curable compound comprising an amino group. This material functions as a condensation polymerization catalyst through the amino group, and also contains a reactive group which can co-react with the silanol-terminated siloxane fluids to become incorporated into the crosslinked siloxane polymer network.

A variety of suitable co-curable compounds comprising an amino group are suitable, and typically these compounds are bi-functional compounds of the general structure: A-B-C, where A is an amino group, B is a linking group, and C is a group that can co-react with the silanol-terminated siloxane fluids, such as an alkoxy-silyl group. Alkoxy-silyl groups are of the general structure (ignoring the other groups bonded to the silicon atom): —Si—OR, where R is alkyl group. These groups can react with water to form a silanol group and an alcohol. The formed silanol groups can react with other silanol groups to form a —Si—O—Si— linkage as described above. This sequence is summarized in Reaction Scheme 1 below:

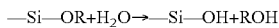

 Reaction Scheme 1

Suitable co-curable compounds comprising an amino group include those described by Formula 2 below:

 Formula 2 wherein each $R^6$ and $R^7$ independently comprises a hydrogen atom or an alkyl, aryl, heteroalkyl, heteroaryl, or aralkyl group; x is an integer of 0, 1, or 2; G is a divalent linking group; each $R^8$ independently is an alkyl, aryl, heteroalkyl, heteroaryl, or aralkyl group; each $R^9$ independently is an alkyl, aryl, heteroalkyl, heteroaryl, or aralkyl group; and y is an integer of 1, 2, or 3.

In some embodiments, x is 2 and $R^7$ is a hydrogen atom, making the amino portion of the compound a primary amine. In other embodiments, x is 1, $R^7$ is a hydrogen atom, and $R^6$ is an alkyl, aryl, heteroalkyl, heteroaryl, or aralkyl group, amking the amino portion of the compound a second amine. In still other embodiments, x is 0, and and $R^6$ is an alkyl, aryl, heteroalkyl, heteroaryl, or aralkyl group, making the amino portion of the compound a tertiary amine. Examples of suitable amino groups include: amino (—$NH_2$); methyl amino (—NHMe); dimethyl amino (—$NMe_2$); ethyl amino (—NHEt); diethyl amino (—$NEt_2$); propyl amino (—NHPr); dipropyl amino (—$NPr_2$); phenyl amino (—NHPh); and the like.

While a wide range of suitable G groups are possible, typically, G is a divalent alkylene group having the general structure: (—$CH_2$—)$_a$ wherein a is an integer of 1 to 18.

A wide range of alkoxy-silyl groups —Si(OR$^8$)$_y$R$^9{}_{3-y}$ are suitable. Typically, $R^8$ is an alkyl group with 1-5 carbon atoms, more typically $R^8$ is a methyl or ethyl group; $R^9$ is an alkyl group with 1-5 carbon atoms, more typically $R^9$ is a methyl or ethyl group; and y is 1 or 2. Examples of suitable alkoxy-silyl groups include: methoxy dimethyl silyl; methoxy diethyl silyl; dimethoxy methyl silyl; dimethoxy ethyl silyl; ethoxy dimethyl silyl; ethoxy diethyl silyl; diethoxy methyl silyl; diethoxy ethyl silyl; and the like.

Examples of suitable commercially available co-curable compounds comprising an amino group include for example, aminopropyltriethoxy silane and aminopropyldiethoxymethyl silane.

A variety of optional additives can also be added to the curable mixture as long as they do not interfere with curing reaction or the desired properties of the gel adhesive. As stated above, the gels may include on or more unreacted silanol fluid. Aditionally, the gels may include one or more additives such as plasticizing agents, colorants, antioxidants, biocides, fillers, and the like.

The gels of this disclosure can be used to prepare a wide range of articles, especially medical articles. These articles include a wide range of adhesive articles as well as medical sealant articles.

The adhesive articles include a substrate and a layer of adhesive gel disposed on at least a portion of at least one major surface of the substrate, where the adhesive gel comprises the adhesive gels described above.

A wide range of substrates are suitable, including release liners, and medical substrates. Release liners are sheet materials that have a low adhesion coating on at least one surface. The gels of the present disclosure can be disposed on a release liner to generate an article comprising a layer of gel on a release liner. This gel/release liner article can be used to prepare other gel/substrate articles by laminating the gel layer to different substrate and then removing the release liner. This permits the gel to be disposed onto substrates to which it is difficult to directly dispose the gel. The gel/release liner article may also be used to apply the gel adhesive layer to an article such as, for example, an electrode, an ostomy device, or the like.

Exemplary medical substrates include polymeric materials, plastics, natural macromolecular materials (e.g., collagen, wood, cork, and leather), paper, cloth, metals, glass, ceramics, and composites. The medical substrate may be a tape backing Examples of suitable tape backings include breathable conformable backing, on which the gel is disposed. A wide range of breathable conformable backings are suitable for use in articles of this disclosure. Typically the breathable conformable backing comprises a woven or knit textile, a nonwoven, or a plastic.

In some embodiments, the breathable conformable backing comprises a high moisture vapor permeable film backings Examples of such backings, methods of making such films, and methods for testing their permeability are described, for example, in U.S. Pat. Nos. 3,645,835 and 4,595,001. Typically such backings are porous materials.

Generally the backing is conformable to anatomical surfaces. As such, when the backing is applied to an anatomical surface, it conforms to the surface even when the surface is moved. Generally, the backing is also conformable to animal anatomical joints. When the joint is flexed and then returned to its unflexed position, the backing stretches to accommodate the flexion of the joint, but is resilient enough to continue to conform to the joint when the joint is returned to its unflexed condition.

Examples of particularly suitable backings can be found in U.S. Pat. Nos. 5,088,483 and 5,160,315, and include elastomeric polyurethane, polyester, or polyether block amide films. These films have a combination of desirable properties including resiliency, high moisture vapor permeability, and transparency.

The gel may be of any suitable thickness. Because the materials are room temperature curable and do not require the input of radiation, a broad range of thicknesses are suitable. In some embodiments, the thickness will be at least 10 micrometers, up to 2 millimeters, and in some embodiments the thickness will be at least 20 micrometers up to 1 millimeter thick. A wide range of intermediate thicknesses are also suitable, such as 100-500 micrometers, 200-400 micrometers, and the like.

A number of different types of medical sealant articles are included in this disclosure. Among the sealant articles are included tissue sealants where a cured layer of the gels of this disclosure applied to a surface, such as the surface of a wound, an incision, and the like. The medical sealants of this disclosure are particularly suitable with medical dressings that are used to provide negative pressure wound therapy as described, for example, in US Patent Publication No. 2011/0106030 (Scholz). In these negative pressure wound therapy dressings, the sealants of this disclosure can provide a sealed environment over a wound to permit fluids to be removed from the sealed environment of the wound.

Also disclosed are methods for preparing medical articles. These medical articles include the gels described above, where the gel can be an adhesive or a sealant. The method includes providing a condensation curable gel precursor composition, applying the condensation curable gel precursor composition to a substrate, and permitting the condensation curable gel precursor composition to cure at room temperature to form a gel. The curable gel precursor compositions have been described in detail above.

In embodiments where the gel is a sealant, the substrate is a surface, such as the surface of a wound, incision or the like, and providing a condensation curable gel precursor composition comprises mixing together of a 2 part mixture. This 2 part mixture comprises: 1) 0.5-45% by weight silicone resin comprising at least two hydroxyl groups; and 99.5-55% by weight of at least one silanol-terminated siloxane fluid; and 2) a co-curable compound comprising an amino group. Parts 1) and 2) are kept physically isolated from each other prior to mixing.

In embodiments where the gel is an adhesive, the substrate comprises a release liner or a medical substrate. Release liners and suitable medical substrates, including tape backings, have been described above.

In some embodiments, medical articles are prepared by disposing the condensation curable gel precursor composition on a release liner, permitting the condensation curable gel precursor composition to cure on the surface of the release liner, and then laminating the cured gel to another substrate or a surface. The substrate may be a medical substrate as described above, or it may the surface of an article such as an electrode, an ostomy device, or the like.

While the condensation curable compositions of this disclosure are room temperature curable, if desired, the compositions can be exposed to an external energy source to, for example, facilitate curing. In some embodiments, it may be desirable to expose the condensation curable gel precursor composition to ultra-violet radiation, gamma radiation, or an electron beam.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wis. unless otherwise noted. The following abbreviations are used: cm=centimeters; mm=millimeters; g=grams; kg=kilograms; lb=pounds; sec=seconds; min=minutes. The terms "weight %", "% by weight", and "wt %" are used interchangeably.

Table of Abbreviations

| Abbreviation or Trade Designation | Description |
|---|---|
| MQ Resin | TMS 803 resin, commercially available from Wacker Chemie AG, Munich, Germany. |
| ST-PDMS | Silanol terminated PDMS (polydimethyl siloxane), commercially available as XIAMETER OHX-4070, from Dow Corning, Midland, MI. |
| APTS | Aminopropyltriethoxy silane |
| APDM | Aminopropyldiethoxymethyl silane, commercially available from Alfa Aesar, Ward Hill, MA |
| Silica | Fumed silica commercially available as TS720 from Cabot Corporation, Boston MA |
| HF-PDMS | Hydroxy functional PDMS commercially available as 350N from Wacker Chemie AG, Munich, Germany |
| Polyurethane Film | Polyurethane polymer film described as "Backing Layer" in U.S. Patent Publication No. 2011/0112458 (Holm et al.) paragraph [0130]. |

TEST METHODS

Tack

Tack was measured using a TA.XT Plus Texture Analyzer (Stable Micro Systems Ltd., Surrey, UK) equipped with a 6 mm diameter polypropylene cylinder probe. The adhesive sample was slit to a width of 1.9 cm and length of 10.2 cm and laminated to a brass bar with 10 mm diameter holes through it to allow for the probe to reach the adhesive face of the tape. The probe speed was set to 1 mm/sec; the force was set to 100 grams; and the contact time was set to 5 seconds. Tack was measured in grams (g).

180° Peel Adhesion

The Peel Adhesion was measured according to the procedure described in ASTM D 3330-90. Peel adhesion was measured using an IMass 2000 peel tester (Imass, Inc., Accord, Mass.). The adhesive sample tape was slit to a width of 1.3 cm and length of 12.7 cm. The resulting tape was then applied to a clean stainless steel panel using four passes of a 2 kg (4.5 lb) hard rubber roller. The sample was equilibrated for 20 minutes at room temperature (22° C.) and 50% relative humidity prior to testing. The panel was then mounted on the bed of the tester and the tape was pulled off at a 180° angle at a speed of 30.5 cm/minute. Results were measured in grams/cm (g/cm).

Shear Holding Power

The Shear Holding Power was measured according to the procedure described in ASTM D 3654-88. The adhesive sample tape with length of 2.54 cm and width of 1.27 cm was laminated to a stainless steel panel measuring 2.54 cm by 5.08 cm such that the tape edges were coextensive with edges of the panels. The panel overlapped 1.27 cm to cover the tape and the free ends of the panels extended in opposite directions. One end of a panel was hung on a rack at room temperature with a 50 gram weight hanging from the bottom of the end of the tape so that the tape sample was under shear stress. The time for the bottom panel to release from the hanging panel was monitored for up to 10,000 minutes. Time to failure was recorded in minutes.

EXAMPLES

Example 1 (E-1)

To 100 parts ST-PDMS was added 45 parts MQ Resin and 1 part APTS. This was mixed with a SPEEDMIXER (Flack- Tek Inc., Landrum, S.C.) for about four minutes and coated on a Polyurethane Film with a knife coater with a 152 micrometer gap. The coated film became a self-tacky silicone gel adhesive tape after 24 hours at room temperature.

Example 2 (E-2)

To 100 parts ST-PDMS was added 45 parts MQ Resin and 1 part APDM. This was mixed with a SPEEDMIXER for about four minutes and coated on a Polyurethane Film with a knife coater with a 152 micrometer gap. The coated film became self tacky silicone gel adhesive tape after 24 hours at room temperature.

Examples 3-10 (E-3-E-10)

Example E-3 through E-10 were prepared according to the procedures described in Example 2 above with the components shown in Table 1. As noted, several coated films were irradiated with 6 mrads of eBeam radiation from a Model CB-300 electron beam generating apparatus (available from Energy Sciences, Inc., Wilmington, Mass.). Silica was mixed with the ST-PDMS and MQ resin in the high speed mixer as noted. Peel Adhesion was measured using the Test Method described above.

Comparative Examples C-1-C-9

Comparatives C-1 through C-9 were prepared as described in Example 2 above with the components in Table 1. Peel Adhesion was measured using the Test Method described above.

TABLE 1

| | Gel Composition (parts) | | | | | |
|---|---|---|---|---|---|---|
| Samples | ST-PDMS | MQ Resin | Silica | APDM | e-Beam | Peel (g/cm) |
| EXAMPLES | | | | | | |
| E-3 | 100 | 5 | 2 | 1.0 | No | 13.4 |
| E-4 | 100 | 5 | 2 | 1.0 | Yes | 4.5 |
| E-5 | 100 | 5 | 2 | 0.2 | No | 27.9 |
| E-6 | 100 | 5 | 2 | 0.2 | Yes | 3.3 |
| E-7 | 100 | 5 | 0 | 1.0 | No | 3.3 |
| E-8 | 100 | 5 | 0 | 1.0 | Yes | 3.3 |
| E-9 | 100 | 5 | 0 | 0.2 | No | 48.0 |
| E-10 | 100 | 5 | 0 | 0.2 | Yes | 3.3 |
| COMPARATIVES | | | | | | |
| C-1 | 100 | 0 | 0 | 0 | Yes | 84.8 |
| C-2 | 100 | 0 | 0 | 1.0 | No | 4.5[a] |
| C-3 | 100 | 0 | 0 | 1.0 | Yes | 72.5 |
| C-4 | 100 | 0 | 0 | 0.2 | No | 3.3[a] |
| C-5 | 100 | 0 | 0 | 0.2 | Yes | 54.7 |
| C-6 | 100 | 0 | 2 | 1.0 | No | 3.3[a] |
| C-7 | 100 | 0 | 2 | 1.0 | Yes | 41.3 |
| C-8 | 100 | 0 | 2 | 0.2 | No | 3.3[a] |
| C-9 | 100 | 0 | 2 | 0.2 | Yes | 10.0 |

[a]= cohesive failure during test

Examples 11-16 and Comparative Examples C-10-C-12

Examples 11 through 16 and Comparative Examples C-10 through C-12 were prepared in toluene (50% solids) in the amounts shown in Table 2, mixed with the SPEEDMIXER, coated on a Polyurethane Film, and dried at 66° C. for 15 minutes. The Comparative Examples were irradiated with 6 mrads e-Beam radiation after drying. Tack, Peel Adhesion, and Shear Holding Power were measured using the Test Methods described above.

TABLE 2

| | Gel Composition (%) | | | | Test Results | | |
|---|---|---|---|---|---|---|---|
| Sample | HF-PDMS | MQ Resin | APTS | Coating (μm) | Tack (g) | Peel (g/cm) | Shear (min) |
| EXAMPLES | | | | | | | |
| E-11 | 77 | 23 | 0.1 | 51 | 2,653 | 9.4 | 5,311 |
| E-12 | 77 | 23 | 0.1 | 152 | NT | NT | 10,000 |
| E-13 | 69 | 31 | 0.1 | 102 | 4,425 | 15.6 | NT |
| E-14 | 62 | 39 | 0.1 | 51 | 4,056 | 14.8 | NT |
| E-15 | 62 | 39 | 0.1 | 152 | 5,758 | 25.9 | NT |
| E-16 | 50 | 50 | 0.1 | 51 | NT | NT | NT |
| COMPARATIVES | | | | | | | |
| C-10 | 77 | 23 | 0 | 102 | 1,792 | 8.0 | 47 |
| C-11 | 50 | 50 | 0 | 51 | 4,418 | 25.3 | 6,858 |
| C-12 | 100 | 0 | 0.1 | 51 | 1,042 | NT | NT |

NT = Not Tested

What is claimed is:

1. A gel composition comprising the reaction product of a condensation curable mixture comprising:
   at least 0.5 to less than 45% by weight silicone resin comprising at least two hydroxyl groups;
   at least 55 to less than 99.5% by weight of at least one silanol-terminated siloxane fluid; and
   a co-curable compound comprising an amino group, wherein the condensation curable mixture is curable at room temperature and wherein the condensation curable mixture upon curing is a gel selected from a medical gel adhesive or a medical gel sealant, wherein the gel comprises a crosslinked matrix containing a liquid or fluid.

2. The gel composition of claim 1, wherein the co-curable compound comprising an amino group has the general structure:

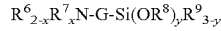
$$R^6_{2-x}R^7_xN\text{-}G\text{-}Si(OR^8)_yR^9_{3-y}$$

wherein each $R^6$ and $R^7$ independently comprises a hydrogen atom or an alkyl, aryl, heteroalkyl, heteroaryl, or aralkyl group;
   x is an integer of 0, 1, or 2;
   G is a divalent linking group;
   each $R^8$ independently is an alkyl, aryl, heteroalkyl, heteroaryl, or aralkyl group;
   each $R^9$ independently is an alkyl, aryl, heteroalkyl, heteroaryl, or aralkyl group; and
   y is an integer of 1, 2, or 3.

3. The gel composition of claim 2, wherein G is a divalent alkylene group having the general structure:

$$(\text{---}CH_2\text{-})_a$$

wherein a is an integer of 1 to 18.

4. The gel composition of claim 1, further comprising at least one non-reactive siloxane fluid.

5. The gel composition of claim 1, wherein the gel composition comprises a medical gel sealant.

6. The gel composition of claim 1, wherein the gel composition comprises a medical gel adhesive layer.

7. The gel composition of claim 1, wherein the gel composition comprises at least 0.5% by weight of extractable siloxane fluid.

8. An article comprising:
a substrate; and
a layer of adhesive gel disposed on at least a portion of at least one major surface of the substrate, the adhesive gel comprising the reaction product of a condensation curable mixture comprising:
  at least 0.5 to less than 45% by weight silicone resin comprising at least two hydroxyl groups;
  at least 55 to less than 99.5% by weight of at least one silanol-terminated siloxane fluid; and
  a co-curable compound comprising an amino group, wherein the condensation curable mixture is curable at room temperature, and wherein the gel comprises a crosslinked matrix and a liquid or fluid.

9. The article of claim 8, wherein the co-curable compound comprising an amino group has the general structure:

$$R^6_{2-x}R^7_xN-G-Si(OR^8)_yR^9_{3-y}$$

wherein each $R^6$ and $R^7$ independently comprises a hydrogen atom or an alkyl, aryl, heteroalkyl, heteroaryl, or aralkyl group;
x is an integer of 0, 1, or 2;
G is a divalent linking group;
each $R^8$ independently is an alkyl, aryl, heteroalkyl, heteroaryl, or aralkyl group;
each $R^9$ independently is an alkyl, aryl, heteroalkyl, heteroaryl, or aralkyl group; and
y is an integer of 1, 2, or 3.

10. The article of claim 9, wherein G is a divalent alkylene group having the general structure:

$$(-CH_2-)_a$$

wherein a is an integer of 1 to 18.

11. The article of claim 8, wherein the adhesive gel further comprises at least one non-reactive siloxane fluid.

12. The article of claim 8, wherein the substrate comprises a release liner or a medical substrate.

13. The article of claim 8, wherein the reaction product of the condensation curable mixture has been exposed to ultra-violet radiation, gamma radiation, or an electron beam.

14. A method of preparing a medical article comprising:
providing a condensation curable gel precursor composition comprising:
  at least 0.5 to less than 45% by weight silicone resin comprising at least two hydroxyl groups;
  at least 55 to less than 99.5% by weight of at least one silanol-terminated siloxane fluid; and
  a co-curable compound comprising an amino group, wherein the condensation curable gel precursor composition is curable at room temperature;
applying the condensation curable gel precursor composition to a substrate; and
permitting the condensation curable gel precursor composition to cure at room temperature to form a gel.

15. The method of claim 14, wherein providing the condensation curable gel precursor composition comprises mixing together of a 2 part mixture, the 2 part mixture comprising:
  1) the at least 0.5 to less than 45% by weight silicone resin comprising at least two hydroxyl groups the; at least 55 to less than 99.5% by weight of at least one silanol-terminated siloxane fluid; and
  2) the co-curable compound comprising an amino group, wherein 1) and 2) are physically isolated from each other prior to mixing.

16. The method of claim 15, wherein the gel comprises a sealant.

17. The method of claim 14, wherein the gel comprises an adhesive.

18. The method of claim 17, wherein the substrate comprises a release liner or a medical substrate.

19. The method of claim 18, wherein the substrate comprises a release liner, and the method further comprises laminating the gel to a second substrate or to a surface.

20. The method of claim 14, wherein the co-curable compound comprising an amino group has the general structure:

$$R^6_{2-x}R^7_xN-G-Si(OR^8)_yR^9_{3-y}$$

wherein each $R^6$ and $R^7$ independently comprises a hydrogen atom or an alkyl, aryl, heteroalkyl, heteroaryl, or aralkyl group;
x is an integer of 0, 1, or 2;
G is a divalent linking group;
each $R^8$ independently is an alkyl, aryl, heteroalkyl, heteroaryl, or aralkyl group;
each $R^9$ independently is an alkyl, aryl, heteroalkyl, heteroaryl, or aralkyl group; and
y is an integer of 1, 2, or 3.

21. The method of claim 14, wherein the gel further comprises at least one non-reactive siloxane fluid.

22. The method of claim 14, further comprising exposing the condensation curable gel precursor composition to ultra-violet radiation, gamma radiation, or an electron beam.

* * * * *

UNITED STATES PATENT AND TRADEMARK OFFICE
CERTIFICATE OF CORRECTION

PATENT NO. : 10,294,333 B2  
APPLICATION NO. : 14/650608  
DATED : May 21, 2019  
INVENTOR(S) : Liu et al.

Page 1 of 1

It is certified that error appears in the above-identified patent and that said Letters Patent is hereby corrected as shown below:

In the Specification

Column 1  
Line 3, Below "GELS" insert -- Cross Reference to Related Applications  
This application is a national stage filing under 35 U.S.C. 371 of PCT/US2013/073070, filed Dec. 4, 2013, which claims priority to U.S. Provisional Application No. 61/736107, filed Dec. 12, 2012, the disclosure of which is incorporated by reference in its/their entirety herein. --.

Column 2  
Line 4, Delete "tht" and insert -- that --, therefor.  
Line 25, Delete "polyoransiloxane" and insert -- polyorganosiloxane --, therefor.

Column 5  
Line 57-58, Delete "poloxyyalkylenes" and insert -- polyoxyalkylene --, therefor.

Column 9  
Line 40, Delete "amking" and insert -- making --, therefor.  
Line 41, Delete "and and" and insert -- and --, therefor.

Column 10  
Line 2, Delete "Aditionally," and insert -- Additionally, --, therefor.  
Line 30, Delete "backing" and insert -- backing. --, therefor.  
Line 37-38, Delete "backings" and insert -- backings. --, therefor.

Signed and Sealed this  
Fourteenth Day of April, 2020

Andrei Iancu  
*Director of the United States Patent and Trademark Office*